United States Patent [19]

Ogawa et al.

[11] Patent Number: 5,414,368
[45] Date of Patent: May 9, 1995

[54] DIELECTRIC CONSTANT DETECTING APPARATUS

[75] Inventors: Kenji Ogawa; Hiroyoshi Suzuki, both of Hyogo, Japan

[73] Assignee: Mitsubishi Denki Kabushiki Kaisha, Tokyo, Japan

[21] Appl. No.: 942,853

[22] Filed: Sep. 10, 1992

[30] Foreign Application Priority Data

Sep. 10, 1991 [JP] Japan ............... 3-230014

[51] Int. Cl.⁶ .................. G01R 27/26; G01N 27/22; G01N 33/22
[52] U.S. Cl. .................. 324/675; 324/682; 324/683; 324/76.79; 73/61.43
[58] Field of Search ............... 324/674, 675, 681, 682, 324/683, 76.77, 76.79; 73/61.43, 61.61; 340/658; 328/155; 331/135, 167

[56] References Cited

U.S. PATENT DOCUMENTS

| | | | |
|---|---|---|---|
| 4,905,655 | 3/1990 | Maekawa | 123/494 |
| 5,005,402 | 4/1991 | Pischinger et al. | 73/61.10 R |
| 5,091,704 | 2/1992 | Kopera | 324/682 X |
| 5,150,062 | 9/1992 | Takeuchi | 324/675 |
| 5,225,783 | 7/1993 | Suzuki et al. | 324/655 |
| 5,313,168 | 5/1994 | Ogawa | 73/61.43 X |
| 5,337,017 | 8/1994 | Ogawa | 324/682 |

FOREIGN PATENT DOCUMENTS

| | | |
|---|---|---|
| 3518186 | 11/1986 | Germany . |
| 62-25248 | 2/1987 | Japan . |
| 2201150 | 8/1990 | Japan . |
| 322488 | 1/1991 | Japan . |

OTHER PUBLICATIONS

English Language Abstract of Japanese Patent Unexamined Publication No. Sho. 62-25248, Shiyouzou Hara, Feb. 3, 1987, p. 591.

Primary Examiner—Kenneth A. Wieder
Assistant Examiner—Glenn W. Brown
Attorney, Agent, or Firm—Sughrue, Mion, Zinn, Macpeak & Seas; Richard C. Turner; Grant K. Rowan

[57] ABSTRACT

A dielectric constant detecting apparatus comprises an LC circuit for shifting the phase of a high frequency voltage signal according to the dielectric constant of a liquid which passes between the coil and the electrode of the LC circuit. A resistor is connected between the LC circuit and at least one part of a phase comparator. The phase comparator detects the phase shift between high frequency signals provided at both ends of the resistor. The resistor and at least one part of the phase comparator are integrally included in an insulator. The output of the phase comparator is compared with a predetermined phase shift value. A voltage control device adjusts the high frequency voltage signal from the voltage applying device so that the phase shift detected by the phase comparator is further adjusted toward the predetermined phase shift value. At least one of the voltage applying device and the voltage control device produces a signal based on the phase shift which is representative of the dielectric constant of the liquid.

6 Claims, 6 Drawing Sheets

DIELECTRIC CONSTANT DETECTING APPARATUS

BACKGROUND OF THE INVENTION

This invention relates to an apparatus which detects in a non-contact mode the dielectric constant of a liquid, e.g. a fuel supplied to a combustor or the like, and more particularly to a fuel dielectric constant detecting apparatus for measuring the alcohol percentage content of a fuel used for the engine of an automobile or the like.

Recently, in USA and in many countries in Europe, in order to decrease the consumption of oil and to reduce the contamination of air by automobile exhaust gas, a fuel prepared by mixing alcohol with gasoline has been being introduced for automobiles. If this alcohol-mixed fuel is used, as it is, for the engine the operation of which is matched with the air-fuel ratio of gasoline fuel, then it is difficult to run the engine smoothly because the alcohol is smaller in stoichiometry than the gasoline, and the air-fuel ratio is therefore altered. Hence, in this case, it is necessary to detect the alcohol percentage content of the alcohol-mixed fuel, thereby to adjust the air-fuel ratio and the ignition timing of the engine.

Heretofore, in order to detect the alcohol percentage content, two systems are available. In one of the system, the dielectric constant of an alcohol-mixed fuel is detected. In the other system, the refractive index thereof is detected. The present applicant has filed an application related to the present invention on an apparatus for detecting the dielectric constant of an alcohol-mixed fuel under Japanese Patent Application No. Hei. 3-22488 which corresponds to U.S. Pat. No. 5,225,783.

FIG. 5 shows an example of the apparatus according to the aforementioned Application. In FIG. 5, a sensor section A includes: a cylindrical insulator 1 in the form of a cylindrical container which is made of insulating material such as oil-resisting plastic into which fuel is introduced; an electrically conductive electrode 3 in the form of a cylinder which is provided inside the cylindrical insulator 1 in such a manner that the cylindrical wall of the electrode 3 is coaxial with and substantially in parallel with the cylindrical wall of the insulator 1; a single layer coil 4 wound on the outer cylindrical surface of the insulator 1 in such a manner that it confronts through the cylindrical wall of the insulator 1 with the electrode 3; and lead wires 4a and 4b connected to the coil 4.

Further in FIG. 5, a fuel passageway 2 is defined by the inner cylindrical surface of the cylindrical insulator 1 and the outer cylindrical surface of the electrode 3; a flange 5 to which the electrode 3 is secured is included, and coupled to the cylindrical insulator 1 through a fuel seal 7, thus providing a fuel container (the flange being integral with the electrode 3); and nipples 6 supply fuel to the fuel passageway 2.

As was described above, in the apparatus, the fuel passageway 2 is located outside the electrode 3, and the single layer coil 4 is located outside the fuel passageway 2 through the cylindrical insulator 1. However, it goes without saying that, even if the order of arrangement of those components is reversed, a fuel container equivalent to the above-described one can be obtained. That is, a sensor section A as shown in FIG. 6 falls in the scope of the invention filed under the aforementioned Japanese Patent Application No. 22488/1991. Now, an apparatus shown in FIG. 6 will be described. In FIG. 6, for convenience in description, parts corresponding functionally to those which have been described with reference to FIG. 5 are therefore designated by the same reference numerals or characters, although they may be different in configuration.

The sensor section A, as shown in FIG. 6, comprises: a cylindrical insulator 1 of oil-resisting plastic which can be formed by injection molding; a single layer coil 4 wound on a cylindrical insulating coil bobbin 4c and sealingly included in the cylindrical insulator 1; lead wires 4a and 4b connected to the single layer coil 4; and an electrically conductive electrode 3 which is substantially in the form of a cylinder provided outside the cylindrical insulator 1. The cylindrical wall of the electrode is substantially in parallel with and coaxial with the cylindrical wall of the single layer coil 4. Both end portions of the electrode 3 are coupled through fuel seals 7 to the cylindrical insulator 1, thus forming a fuel container. A fuel passageway 2 is formed between the inner cylindrical surface of the cylindrical electrode 3 and the wall of an annular recess formed in the cylindrical insulator 1. In the wall of the annular recess, the single layer coil 4 is buried in such a manner that it is spaced a predetermined distance from the electrode 3. Nipples 6 are connected to the electrode 3, to lead fuel into the fuel passageway 2.

Further in FIG. 6, a detecting circuit section B comprises: a resistor 10 connected in series to the lead wire 4a of the single layer coil 4, thus forming a series circuit; a 0° phase comparator to which signals provided at both ends of the resistor 10 are applied; a low-pass filter 12 to which the output of the phase comparator 11 is applied; a comparison integrator 13 to which the output of the low-pass filter 12 and a predetermined reference voltage $V_{ref}$ corresponding to a phase of 0° are applied; a voltage-controlled oscillator 14 to which the output of the comparison integrator 13 is applied; an amplifier 15 for amplifying the output of the voltage-controlled oscillator 14, the output of the amplifier 15 being connected to the aforementioned series circuit; and a frequency divider 16 for dividing the output frequency of the voltage-controlled oscillator 14.

The operation of the conventional apparatus is as follows:

Each of the sensor sections A shown in FIGS. 5 and 6 has an equivalent circuit and characteristics as shown in FIGS. 4 (a),(b) and (c). FIG. 4(a) shows a parallel resonance equivalent circuit; FIG. 4(b) indicates frequencies with sensor section impedances and current-voltage phases; and FIG. 4(c) indicates resonance frequencies with methanol percentage contents.

FIG. 4(a) indicates a current I, a voltage V, an impedance Z, the inductance L of the single layer coil 4, an electrostatic capacitance $C_f$ between the single layer coil 4 and the electrically conductive electrode 3 which changes with the dielectric constant $\epsilon$ of the fuel in the fuel passageway 2; and a capacitance $C_p$ which is unrelated to the dielectric constant $\epsilon$ of the fuel such as a stray capacitance of the lead wire 4a or the input capacitance of the phase comparator. When the signal applied to the lead wire 4a of each of the sensors A shown in FIGS. 5 and 6 is changed in frequency, then a parallel LC resonance occurs as shown in FIG. 4b. In this operation, the parallel resonance frequency $f_r$ can be represented by the following Equation (1):

$$f_r = 1/2\pi \sqrt{L \times (C_p + C_f)} = K/\sqrt{a + b \times \epsilon} \quad (1)$$

where K, a and b are the constants determined from the configuration of the sensor section A.

The resonance frequency $f_r$ depends on the dielectric constant $\epsilon$ of the fuel as is apparent from Equation (1), and it decreases as the dielectric constant $\epsilon$ of the fuel increases. When measured with the apparatus whose sensor was of a predetermined configuration, the resonance frequency $f_r$ was about 7.5 MHz in the case of a methanol having a dielectric constant $\epsilon$ of 33, and 9.5 MHz in the case of a gasoline having a dielectric constant $\epsilon$ of 2. In the cases of mixed fuels prepared by mixing methanol and gasoline optionally, the resonance frequency $f_r$ changed with the methanol percentage content as shown in FIG. 4. Thus, by detecting a signal corresponding to the resonance frequency $f_r$, the dielectric constant $\epsilon$ of the fuel, and accordingly the methanol percentage content of the methanol mixed fuel can be detected.

In each of the FIGS. 5 and 6, the detecting circuit section B is so designed as to detect the above-described resonance frequency $f_r$. Under the condition that the methanol-mixed fuel is flowing in the fuel passageway 2, the voltage-controlled oscillator 14 applies a high frequency signal to the series circuit of the resistor 10 and the single layer coil 4, and high frequency voltage signals at both ends of the resistor 10; that is, a high frequency voltage signal applied to the series circuit and a high frequency voltage signal applied to the single layer coil 4 are applied to the phase comparator 11, where they are subjected to phase comparison. In the case where a high frequency voltage signal having the frequency of which is equal to the resonance frequency $f_r$ is applied to the series circuit, then as shown in the part (b) of FIG. 4 the current-voltage phase of the sensor section A is 0°, and therefore the phase shift between the high frequency voltages at both ends of the resistor 10 is 0°.

On the other hand, in the case where a high frequency voltage signal whose frequency is lower than the resonance frequency $f_r$ is applied to the series circuit, as shown in FIG. 4(b) the current-voltage phase of the sensor section A is ahead of 0°, and therefore the phase shift between the high frequency voltages at both ends of the resistor 10 is larger than 0° with the phase of the high frequency signal as a reference which is applied to the series circuit. Hence, the output of the phase comparator 11 is converted into a DC voltage corresponding to the phase shift with the aid of lowpass filter, and the DC voltage and a reference DC voltage $V_{ref}$ corresponding to a phase shift of 0° are applied to the comparison integrator 13 where the difference between the DC voltage and the reference DC voltage $V_{ref}$ is subjected to integration. The output of the comparison integrator 13 is applied to the voltage-controlled oscillator 14 which applies the high frequency signal to the series circuit through the resistor 10, on thus completing, a phase synchronization loop has been formed.

The voltage-controlled oscillator 14 performs a control operation through the phase synchronization loop so that the phase shift between the high frequency voltage signals at both ends of the resistor 10 may be 0°. Hence, the oscillation frequency of the voltage-controlled oscillator 14 is equal to the resonance frequency $f_r$ at all times. And a frequency output $f_{out}$ is obtained by suitably dividing the output frequency of the voltage-controlled oscillator 14 with the frequency divider 16. Furthermore, since the oscillation frequency of the voltage-controlled oscillator corresponds exactly to the control input voltage, the output of the comparison integrator 13 can be obtained as a voltage output $V_{out}$.

However, in the apparatus shown in FIG. 6, it is difficult to reduce the length of the lead wire 4a of the single layer coil 4, although the stray capacity of the lead wire 4a is relatively large. Employment of a shielded wire as the lead wire 4a is effective in eliminating noise signals; however, it will increase the stray capacitance. Even when the shield is separated from the lead wire 4a, the stray capacitance changes depending on the position where the lead wire 4a lies or on the environmental conditions such as for instance ambient humidity.

Such a large stray capacitance means that, in the above-described Equation (1), $C_p$ increases when compared with $C_f$, and as is apparent from Equation (1), the rate of change of the resonance frequency $f_r$ is decreased with respect to the variation of the dielectric constant $\epsilon$ of the fuel. When the stray capacitance changes depending on the environmental conditions, the resonance frequency $f_r$ is changed even if the dielectric constant $\epsilon$ of the fuel is not changed, which adversely affects the accuracy of detection of the dielectric constant of the fuel.

SUMMARY OF THE INVENTION

Accordingly, this invention has been attained to eliminate the above-described difficulties accompanying a conventional fuel dielectric constant detecting apparatus.

More specifically, an object of the invention is to provide a dielectric constant detecting apparatus in which, with respect to variations in the dielectric constant of a subject (e.g. fuel) under test, the rate of change of the resonance frequency can be maximized, and the resonance frequency can be maintained unchanged even when the environmental conditions change, thus being able to detect the dielectric constant of the fuel with high accuracy.

The foregoing object and other. objects of the invention have been achieved by the provision of an apparatus for detecting a dielectric constant of liquid, said apparatus comprising: means for applying a high frequency voltage signal; means for subjecting the high frequency voltage signal from said voltage control means to resonance corresponding to the dielectric constant of the liquid; a resistor having one end connected to said subjecting means and the other end to which the high frequency voltage signal is applied from said applying means; detecting means connected between said one and the other ends of said resistor for detecting a phase shift between the high frequency signal applied by said applying means and the high frequency voltage signal subjected to resonance by said subjecting means; control means for controlling the high frequency voltage signal from said applying means to adjust the phase shift detected by said detecting means to a predetermined value, at least one of said applying means and control means producing a signal representative of the dielectric constant of the liquid; and an insulator for integrally covering said subjecting means, said resistor and at least one part of said detecting means.

In the apparatus, since the subjecting means, the resistor and at least one part of the phase detecting means are sealingly included in the insulator, the stray capacitance of the conductor connecting the subjecting means, the resistor, and the phase detecting means is minimized.

The nature, principle, and utility of the invention will be more clearly understood from the following detailed description of the invention when read in conjunction with the accompanying drawings.

DETAILED DESCRIPTION OF THE PREFERRED EMBODIMENT

A fuel dielectric constant detecting apparatus, which constitutes one embodiment of this invention, will be described with reference to FIG. 1.

Figure 1:
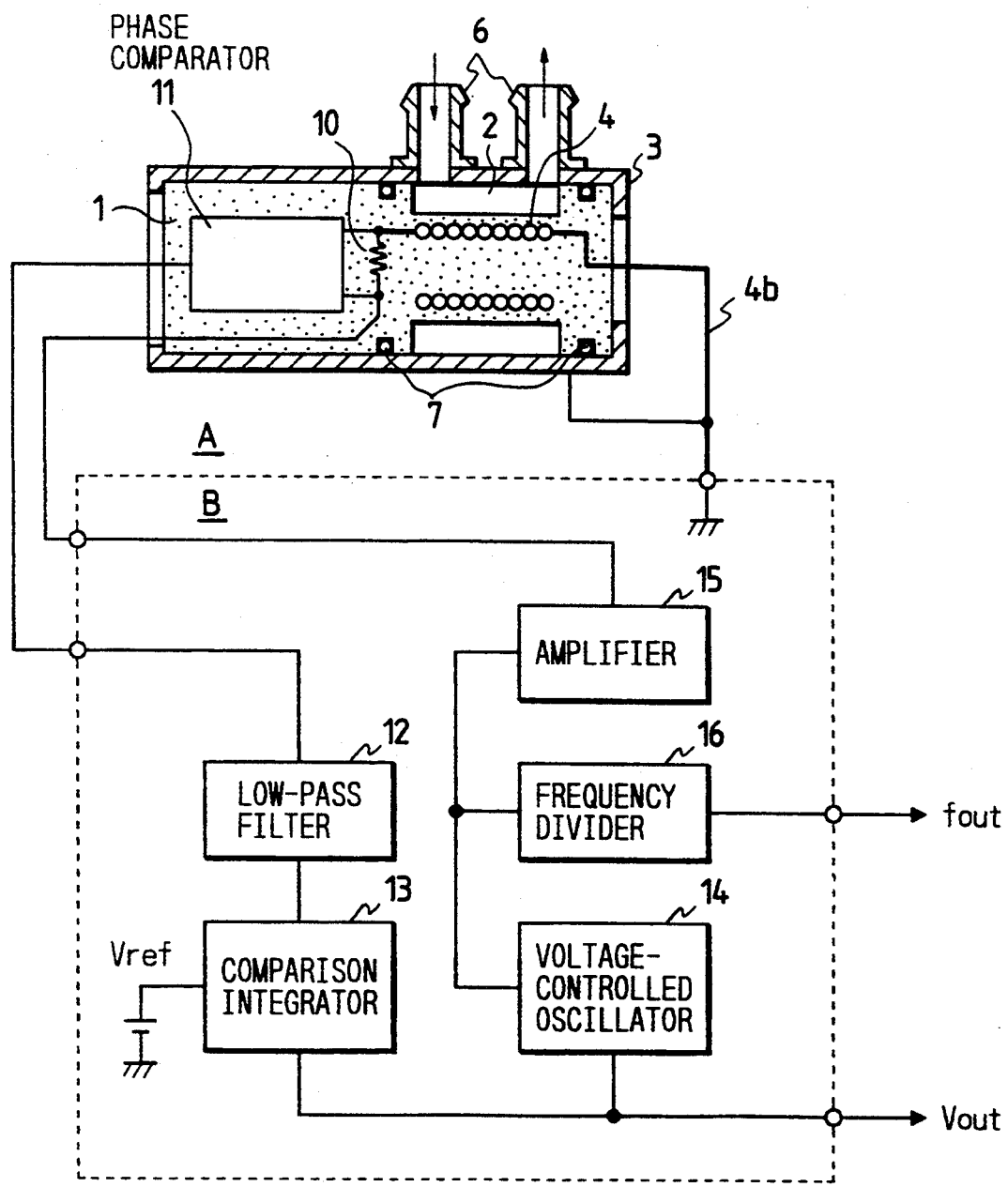
FIG. 1 is an explanatory diagram, partly as a block diagram, showing the arrangement of a fuel dielectric constant detecting apparatus, which constitutes one embodiment of the invention.
Figure 6:
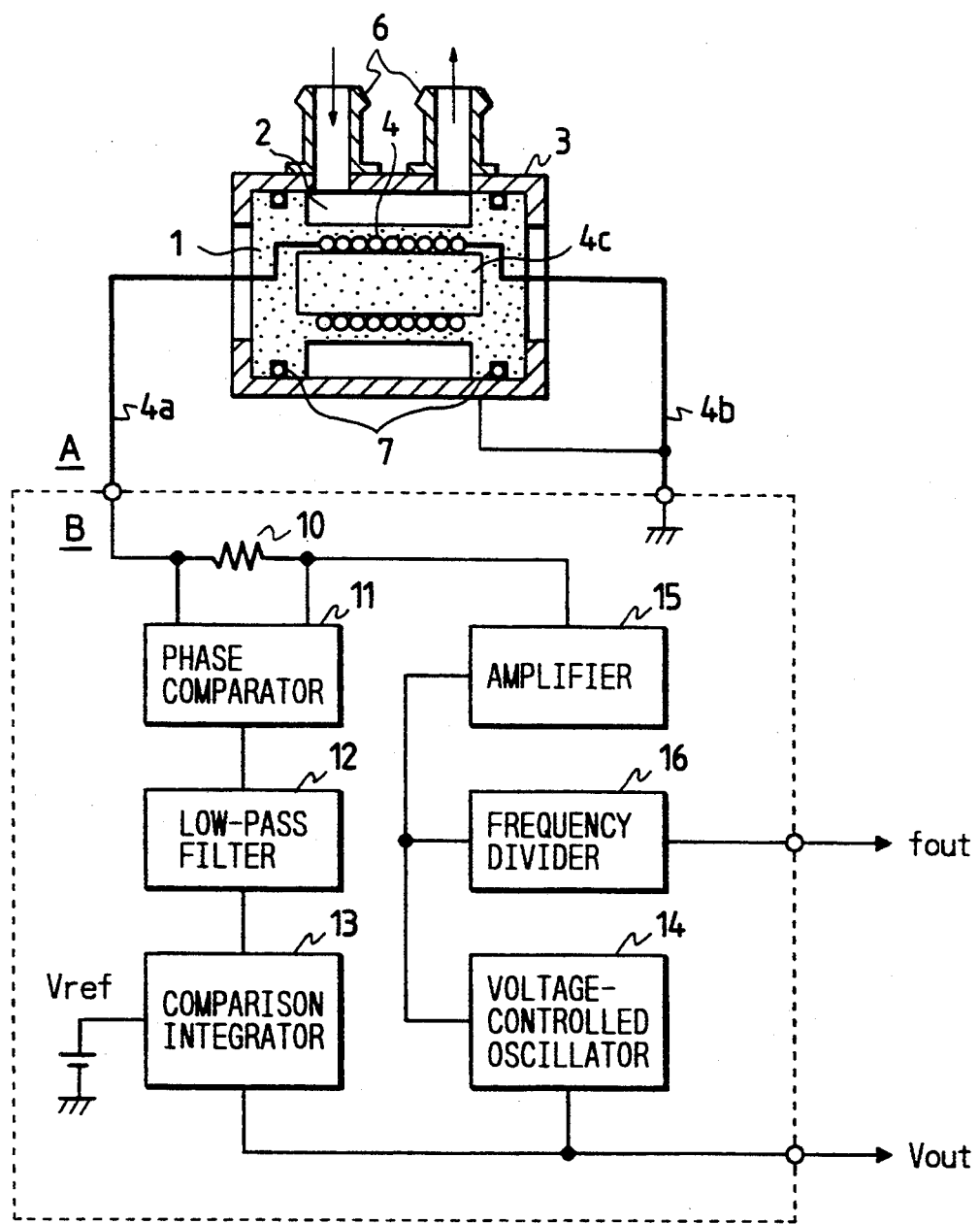
FIG. 6 is an explanatory diagram, partly as a block diagram showing another example of the conventional fuel dielectric constant detecting apparatus.

In FIG. 1, reference numerals 1 through 16 designate parts which correspond functionally to those which have been designated by the same reference numerals in FIG. 6. However, it should be noted that, in the above-described conventional apparatus (FIG. 6), the resistor 10 and the phase comparator 11 are provided in the detecting circuit section B; whereas, in the apparatus of the invention, as shown in FIG. 1, the resistor 10 and the phase comparator 11 are provided in the sensor section A, and they are sealingly buried in the insulator 1 together with the single layer coil 4.

Figure 2:
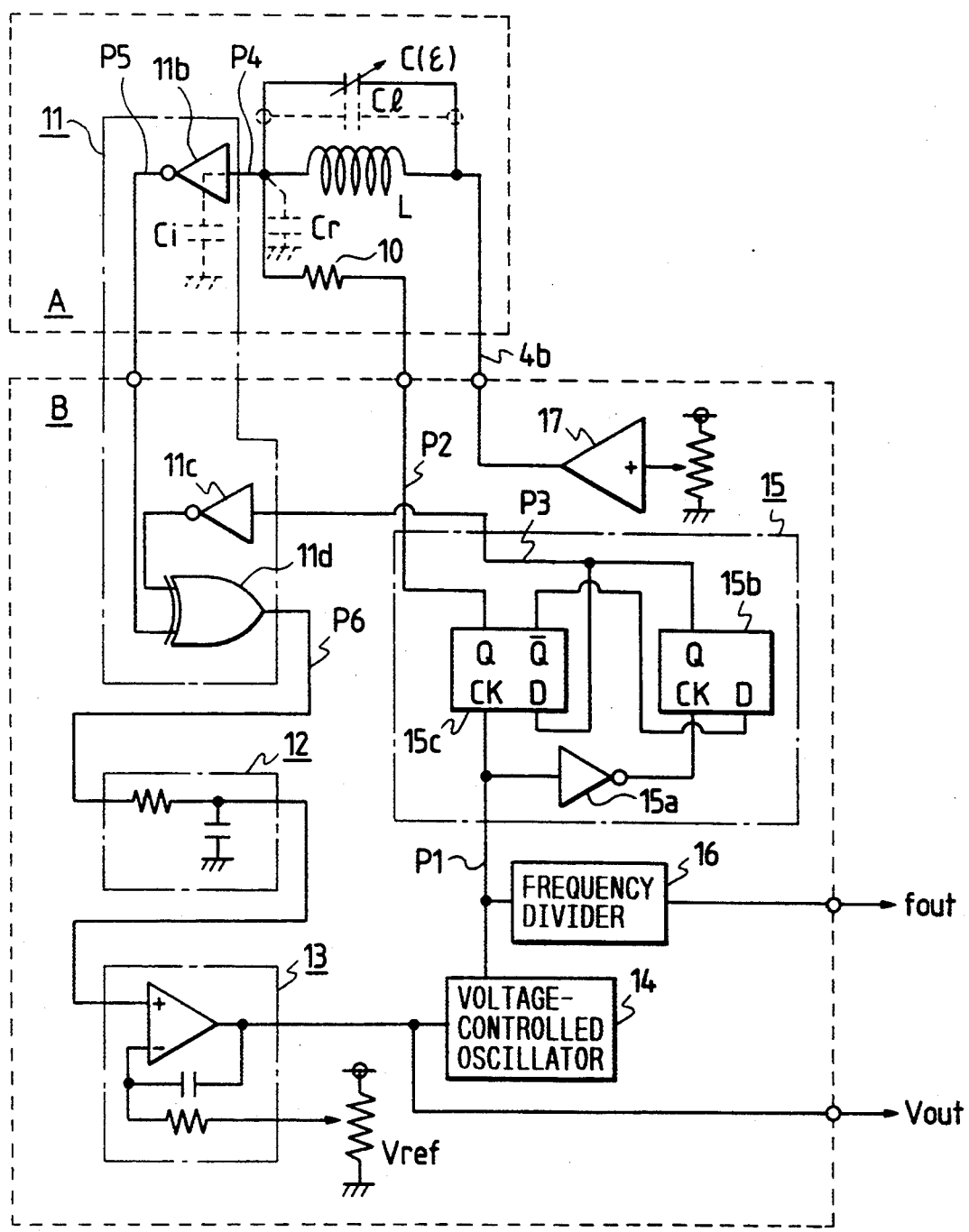
FIG. 2 is a block diagram showing the arrangement of a concrete example of the apparatus shown in FIG. 1.

A concrete example of the fuel dielectric constant detecting apparatus of the invention will be described with reference to FIG. 2. In the concrete example, an EXCLUSIVE OR circuit 11d is employed to form the phase comparator 11, and the phase synchronization loop is such that the phase shift between high frequency voltage signals at both ends of the resistor 10 is 0°. In FIG. 2, the phase comparator 11 comprises: the aforementioned EXCLUSIVE OR circuit 11d, and two inverters 11b and 11c the output terminals of which are connected to the input terminals of the EXCLUSIVE OR circuit 11d. In FIG. 1, the phase comparator 11 is provided, in its entirety, in the sensor section; whereas, in FIG. 2, the inverter 11b, the input terminal of which is connected to the resistor 10 and the single layer coil 4, is provided in the sensor section A, and the inverter 11c and the EXCLUSIVE OR circuit 11d are provided in the detecting circuit section B. However, the arrangement of FIG. 1 is essentially equal to that of FIG. 2 in that, in the case of FIG. 1, the resistor 10, the phase comparator 11, and the single layer coil 4 are provided in the sensor section A, and in the case of FIG. 2, the resistor 10, the inverter 11b of the phase comparator 11, and the single layer coil 4 are provided in the sensor section A, thereby to minimize the stray capacity of the conductors connecting the single layer coil 4, the resistor 10 and the phase comparator 11.

Further in FIG. 2, reference character 15a designates an inverter; and 15c and 15b, first and second D flip-flop circuits, respectively, those circuit elements 15a, 15b and 15c forming the amplifier 15; 17, an operational amplifier. The output terminal of the operational amplifier 17 is connected to the lead wire 4b, and the non-inversion input terminal (+) is connected to the slide contact of a voltage dividing variable resistor. Signals P1 through P6 at various circuit points are as shown in a time chart of FIG. 3.

The operation of the fuel dielectric constant detecting apparatus will be described with reference mainly to FIG. 2.

The high frequency square wave signal P1 outputted by the voltage controlled oscillator 14 is applied to the CK port of the first D flip-flop circuit 15c. The high frequency square wave signal P1 is further applied to the inverter circuit 15a, where it is subjected to phase inversion. The output signal of the inverter circuit 15a is applied to the CK port of the second D flip-flop circuit 15b. A signal provided at the inversion output port of the first D flip-flop circuit 15c is applied to the D port of the second D flip-flop circuit 15b. A signal provided at the output port Q of the second D flip-flop circuit 15b is applied to the D port of the first D flip-flop circuit 15c.

Therefore, the signal P2 at the output port Q of the first D flip-flop circuit 15c, which is the high frequency signal applied to the single layer coil 4 through the resistor 10, is changed at the rise of the above-described high frequency square wave signal P1; that is, it is converted into a signal which is obtained by subjecting the signal P1 to ½ frequency division. The signal P3 at the output port Q of the second D flip-flop circuit 15b, which is applied to one of the input terminals of the EXCLUSIVE OR circuit 11d through the inverter 11c is changed at the fall of the signal P1; that is, it is converted into a signal which is equal in frequency to the above-described signal P2 and different in phase by 90° therefrom.

Figure 3:
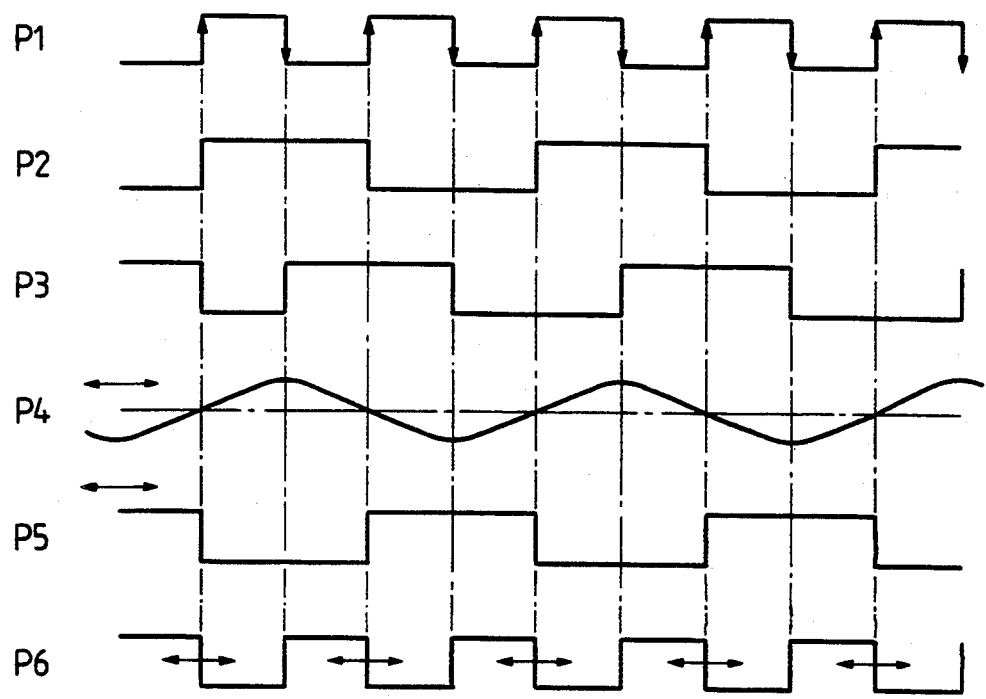
FIG. 3 is a time chart for a description of the operation of the apparatus shown in FIG. 2.

A signal P4 at the connecting point of the resistor 10 and the single layer coil 4, which is applied to the single layer coil 4, is applied through the inverter 11b to the other input terminal of the EXCLUSIVE OR circuit 11d, so that the signal P4 and the signal obtained by inverting the signal P3 are subjected to phase comparison. The high frequency signal P4 provided at the connecting point of the resistor 10 and the single layer coil 4 is sinusoidal as shown in FIG. 3. Therefore, by adjusting the DC level of the signal P4 with the operational amplifier 17 and the variable resistor connected thereto to the decision level of the inverter 11b, the sinusoidal signal P4 can be shaped into a square wave signal P5.

With the resonance frequency of the LC circuit in the sensor section A, the phase of the square wave signal P5 of the inverter 11b is opposite to that of the square wave signal P2 applied to the resistor 10, and is shifted by 90° from that of the signal P3 provided at the output port Q of the second D flip-flop circuit 15b. Therefore, the output of the EXCLUSIVE OR circuit 11d becomes a square wave signal P6 with a duty of 50% when the phase shift between the signals P2 and P4, which are provided at both ends of the resistor 10, is 0°; that is, the EXCLUSIVE OR circuit outputs the square wave signal P6 with the resonance frequency of the LC circuit in the sensor section A.

With frequencies other than the resonance frequency, the duty is less than or more than 50%, and the square wave signal has a duty corresponding exactly to the phase shift between the signals P2 and P4. Therefore, when the output signal P6 of the EXCLUSIVE OR circuit 11d is applied to the low-pass filter 12, the DC output of the latter corresponds exactly to the phase shift between the high frequency voltage signals P2 and P3 provided at both ends of the resistor 10.

The output signal of the low-pass filter 12 is applied to the comparison integrator 13, where the difference between the output signal and the reference voltage $V_{ref}$ is subjected to integration. The reference voltage $V_{ref}$ has been so adjusted with the variable resistor connected to the comparison integrator 13 that its level be equal to the DC level outputted by the low-pass filter 12 when the phase shift between the signals P2 and P3 is 0°. The result of integration; i.e., the output of the comparison integrator 13 is applied to the voltage-controlled oscillator 14, to control the oscillation frequency.

Figure 4A:
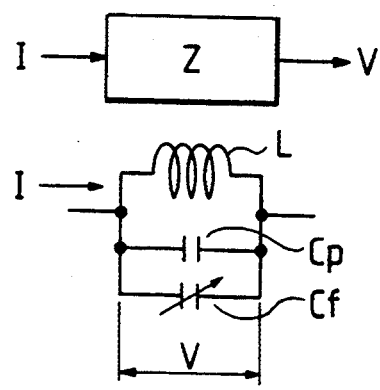
FIG. 4(a) is a circuit diagram showing a parallel resonance equivalent circuit.
Figure 4B:
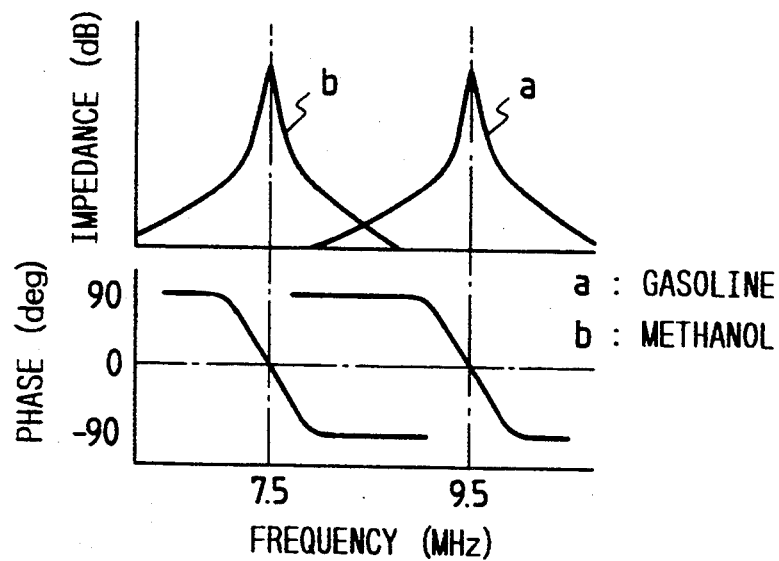
FIG. 4(b) is a graphical representation showing frequencies with sensor section impedances and current-voltage phases.
Figure 4C:
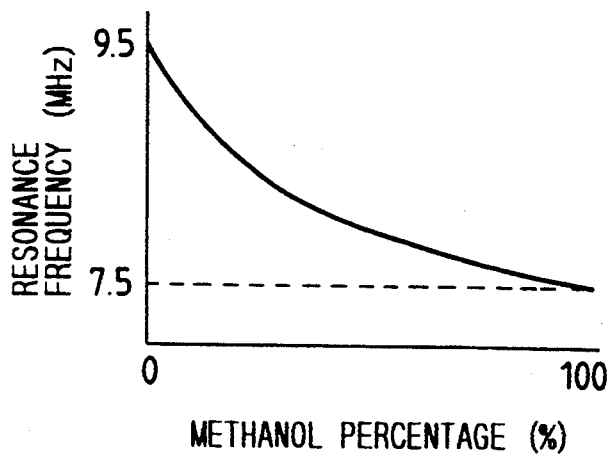
FIG. 4(c) is a graphical representation indicating resonance frequencies with methanol percentage contents.
Figure 5:
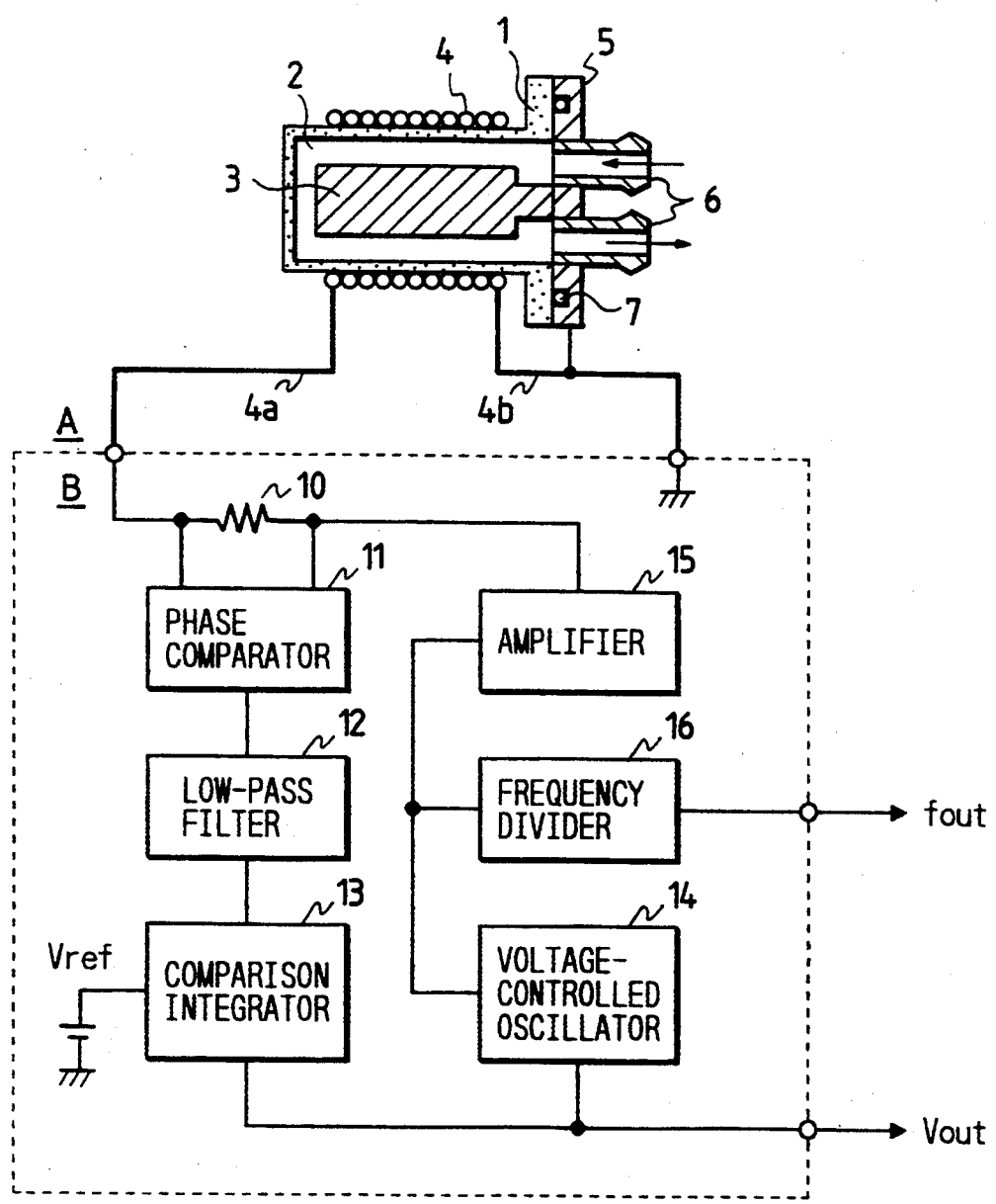
FIG. 5 is an explanatory diagram, partly as a block diagram, showing the arrangement of an example of a conventional fuel dielectric constant detecting apparatus.

The circuit thus designed serves as a phase synchronization loop which controls the output frequency of the voltage-controlled oscillator 14 so that the phase shift between the high frequency voltages signals provided at both ends of the resistor 10 be 0°. Hence, the frequency output $f_{out}$, which is obtained by dividing the frequency of the voltage-controlled oscillator 14 with the frequency divider 16, is a function which decreases monotonously with respect to the dielectric constant $\epsilon$ of the fuel; i.e., the methanol percentage content as shown in FIG. 4(c). It goes without saying that the output of the comparison integrator 13 applied to the voltage-controlled oscillator 14 can be employed as the voltage output The fuel dielectric constant detecting apparatus of the invention is different from the conventional one as follows:

In the apparatus of the present invention, the resistor 10 and the inverter 11b forming a part of the phase comparator 11 are provided in the sensor section A instead of the detecting circuit section B for the following reason: The resonance frequency $f_r$ of the LC circuit in the sensor section A is as indicated by the above-described Equation (1). This Equation (1) can be rewritten into the following Equation (2) by using reference characters in FIG. 2:

$$f_r = 1/2\pi \sqrt{L \times (C_1 + C_i + C_r + C(\epsilon))} \qquad (2)$$

where $C_1$ is the stray capacitance of the single layer coil 4, $C_i$ is the input capacitance of the inverter 11b, $C_r$ is the stray capacitance of the conductor connecting the single layer coil 4, the resistor 10 and the inverter (which corresponds to the stray capacitance of the lead wire 4a in the conventional apparatus in FIG. 6), and $C(\epsilon)$ is the capacitance which changes with the dielectric constant $\epsilon$ of the fuel. The variation in resonance frequency which is due to the variation in capacitance is utilized for detection of the dielectric constant of the fuel, and accordingly the methanol percentage content.

The rate of change of the resonance frequency $f_r$ with respect to the variation of the dielectric constant $\epsilon$ of the fuel is determined from the balance between the sum of the three capacitances $C_1$, $C_i$ and $C_r$ which are independent of the dielectric constant $\epsilon$, and the capacitance $C(\epsilon)$ dependent on the dielectric constant $\epsilon$, as is seen from Equation (2). And the rate of change is increased in accordance with the amount of the capacitance $C(\epsilon)$ exceeding the sum of those capacitances. Accordingly, it is desirable to decrease the capacitances $C_1$, $C_i$ and $C_r$ as much as possible. In the case when, although the capacitance $C(\epsilon)$ is not changed, any one of the capacitances $C_1$, $C_i$ and $C_r$ changes, the resonance frequency is changed. Therefore, the capacitances $C_1$, $C_i$ and $C_r$ should not be changed by environmental conditions such as for instance ambient humidity.

The difference between the apparatus of the invention and the conventional apparatus resides in that the resistor 10 and the inverter 11b forming the phase comparator 11 are provided in the sensor section A instead of the detecting circuit section B. That is, in the invention, the single layer coil 4, the resistor 10, and the inverter 11b are sealingly buried in the insulator 1, so that the length of the conductor (corresponding to the lead wire 4a in the conventional apparatus) is decreased greatly. As a result, the capacitance $C_r$ in FIG. 2 is much smaller than in the conventional apparatus, and it is not changed by environmental conditions such as for instance ambient humidity because, as was described above, the single layer coil 4, the resistor 10 and the inverter 11b are sealingly buried in the insulator 1.

In the above-described embodiment, the inverter forming the phase comparator and the resistor together with the single layer coil are sealingly buried in the insulator. This technical concept may be applied to the remaining components. Furthermore, in the above-described embodiment, the apparatus is to detect the methanol percentage content of a methanol-mixed gasoline; however, it should be noted that the invention is not limited thereto or thereby. That is, the technical concept of the invention may be equally applied to a number of apparatuses for detecting the dielectric constants of other liquids.

As was described above, the apparatus of the invention comprises the electrically conductive electrode, and the detecting coil sealed in the insulator. The detecting coil is spaced a predetermined distance from the electrode so as to pour a fuel under test into the space between the detecting coil and the electrode. The resistor is connected in series to the detecting coil. The phase comparator, the low-pass filter, the comparison integrator, and the voltage-controlled oscillator cooperate to feedback-control the frequency of the signal applied to the detecting coil through the resistor so that the phase shift between the high frequency voltage signals provided at both ends of the resistor be 0°, whereby the alcohol percentage content thereof is detected from the voltage output of the comparison integrator or the output frequency of the voltage-controlled oscillator. In the apparatus thus organized, the resistor and the phase comparator or part of the phase comparator together with the detecting coil are sealingly buried in the insulator. As a result, in the apparatus, the capacitances independent of the dielectric constant of the fuel are minimized. Hence, the variation of the output of the apparatus as to the variation of the dielectric constant of fuel is maximized, and the alcohol percentage content can be detected with high accuracy at all times no matter how the environmental conditions such as for instance ambient humidity changes.

While there has been described in connection with the preferred embodiment of this invention, it will be obvious to those skilled in the art that various changes and modifications may be made therein without departing from the invention, and it is aimed, therefore, to cover in the appended claim all such changes and modifications as fall within the true spirit and scope of the invention.

What is claimed is:

1. An apparatus for detecting a dielectric constant of liquid, said apparatus comprising:

phase shifting means for creating a shifted high frequency voltage signal by shifting a phase of an unshifted high frequency voltage signal by an amount corresponding to said dielectric constant of said liquid;

applying means for applying said unshifted high frequency voltage signal to said phase shifting means;

a resistor having a first end and a second end, wherein said first end of said resistor is connected to said phase shifting means and said second end of said resistor is connected to said applying means;

detecting means connected across said resistor for detecting a phase shift between said shifted high frequency voltage signal created by said phase shifting means and said unshifted high frequency voltage signal applied from said applying means;

control means for adjusting said unshifted high frequency voltage signal from said applying means to adjust said phase shift detected by said detecting means toward a predetermined phase shift value, wherein said dielectric constant of said liquid is represented by at least one of a first dielectric signal produced by said control means which is based on said phase shift detected by said detecting means and a second dielectric signal produced by said applying means which is based on said adjusted unshifted high frequency voltage signal; and an insulator for integrally covering said phase shifting means, said resistor and at least one part of said detecting means.

2. A dielectric constant detecting apparatus according to claim 1, in which said phase shifting means comprises a detecting coil and an electrically conductive electrode which is spaced by a predetermined distance from said detecting coil so as to provide a space therebetween into which said liquid flows, wherein said dielectric constant of said liquid, an inductance of said detecting coil, and a capacitance of said electrically conductive electrode at least partially determine a resonant frequency of said phase shifting means.

3. A dielectric constant detecting apparatus according to claim 1, in which said control means comprises:

a signal converting member which converts an output signal of said detecting means to a direct current voltage signal, wherein said direct current voltage signal corresponds to said phase shift detected by said detecting means;

a comparison integrator which determines a difference between said direct current voltage signal corresponding to said phase shift and a predetermined voltage value corresponding to said predetermined phase shift value, wherein said control means outputs said difference to said applying means to adjust said unshifted high frequency voltage signal applied from said applying means so as to decrease said difference between said direct current voltage signal and said predetermined voltage value.

4. A dielectric constant detecting apparatus according to claim 3, wherein said dielectric constant of said liquid is calculated on the basis of at least one of an output from said applying means and an output from said comparison integrator when said direct current voltage signal of said signal converting member equals said predetermined voltage value.

5. A dielectric constant detecting apparatus according to claim 1, wherein said predetermined phase shift value is 0 degrees.

6. A dielectric constant detecting apparatus according to claim 1, wherein said liquid is fuel including at least one of gasoline and alcohol.

* * * * *